United States Patent [19]

Guth et al.

[11] 4,435,300

[45] Mar. 6, 1984

[54] DETERGENT COMPOSITIONS

[75] Inventors: Jacob J. Guth, Upper Black Eddy, Pa.; Diane L. Spilatro, Piscataway; Robert J. Verdicchio, Succasunna, both of N.J.

[73] Assignee: Johnson & Johnson Baby Products Company, New Brunswick, N.J.

[21] Appl. No.: 375,074

[22] Filed: May 5, 1982

Related U.S. Application Data

[63] Continuation-in-part of Ser. No. 241,874, Mar. 9, 1981, abandoned.

[51] Int. Cl.³ .................. C11D 1/10; C11D 1/65; C11D 1/88; C11D 1/94

[52] U.S. Cl. .................. 252/117; 252/89.1; 252/134; 252/173; 252/174; 252/174.19; 252/174.21; 252/545; 252/546; 252/557; 252/DIG. 5; 252/DIG. 13; 252/DIG. 14; 260/401; 260/403; 260/404; 260/413; 424/70; 424/318; 424/319

[58] Field of Search ........ 260/401, 403, 404, 404.5 R; 252/DIG. 5, DIG. 7, DIG. 13, 89.1, 117, 544, 545, 546, 557; 424/70, 316, 318, 319

[56] References Cited

U.S. PATENT DOCUMENTS

| | | | |
|---|---|---|---|
| 2,781,382 | 2/1957 | Mannheimer | 260/401 |
| 2,781,391 | 2/1957 | Mannheimer | 252/545 X |
| 3,086,943 | 4/1963 | Lang | 252/557 X |
| 3,779,933 | 12/1973 | Eisen | 252/118 |
| 3,926,863 | 12/1975 | Perla | 252/557 |
| 4,277,378 | 7/1981 | Tsujii | 252/546 |
| 4,303,543 | 12/1981 | Mansy | 252/117 |

OTHER PUBLICATIONS

Riso, Richard R., "Protein Detergents", Published by Stepan Chemical Co., Maywood Division, Maywood, N.J. 1963, 8 pp.

*Primary Examiner*—Dennis L. Albrecht
*Attorney, Agent, or Firm*—Steven P. Berman

[57] ABSTRACT

An improved low irritating detergent and cleansing composition exhibiting good foam properties is disclosed. The composition is a synergistic mixture of an amphoteric-fatty acid complex and an anionic surfactant containing at least one carboxylic acid moiety.

9 Claims, No Drawings

DETERGENT COMPOSITIONS

REFERENCE TO RELATED APPLICATION

This is a continuation-in-part of copending application Ser. No. 241,874, filed Mar. 9, 1981 now abandoned.

BACKGROUND OF THE INVENTION

Detergent and cleansing compositions intended for use as personal cleansing products not only must exhibit good cleansing and foam characteristics but they must also be non-irritating or have low irritation potential to the skin and the eyes.

Synthetic detergents which are useful in such detergent and cleansing compositions are well known in the art and include anionic, cationic, amphoteric and nonionic detergents or surfactants, as they are usually referred to. The surfactants generally exhibiting the more superior properties in terms of foaming, cleaning and end result attributes are the nonionic detergents. Thus, most detergent and cleansing formulations intended for personal use contain anionic surfactants as one of the active ingredients. These surfactants, however, have a tendency to be very irritating to the skin and the eyes in the levels normally utilized, i.e., above 10% by weight of the total composition. For this reason, detergent compositions intended for personal use containing anionic surfactants are modified by substituting a significant amount of nonionic surfactants which are generally mild although of less effective foaming and cleansing ability. Certain amphoteric surfactants have also been reported to have a low eye irritation potential. Although numerous detergent and cleansing compositions are available commercially, there is still a need for compositions in which irritancy can be substantially eliminated without sacrificing other desired properties such as cleansing and foaming attributes.

Several U.S. patents describe compositions in which both amphoteric and nonionic surfactants are incorporated in detergent compositions containing anionic surfactants. Thus, in U.S. Pat. Nos. 2,999,069 an 3,055,836 there are described shampoo compositions comprising certain mixtures of ethoxylated anionic, amphoteric and polyethoxylated nonionic surfactants. Further, in U.S. Pat. No. 3,928,251 there are described shampoo compositions comprising certain mixtures of anionic, nonionic and zwitterionic surfactants. Similarly, in U.S. Pat. No. 3,950,417 shampoo compositions are described for which low ocular irritancy is claimed. In these compositions, nonionic and amphoteric surfactants have been added to modify anionic surfactants. All of these compositions include a nonionic surfactant as an essential component as well as an anionic surfactant and as mentioned above, these surfactants have various negatives.

It is, therefore, an object of this invention to provide improved detergent and cleansing compositions.

It is a further object of this invention to provide improved detergent and cleansing compositions which exhibit low irritation potential to the eyes and skin.

It is a further object of this invention to provide improved detergent and cleansing compositions which exhibit good foaming properties including excellent foam stability.

Other objects of this invention will be set forth in or be apparent from the following detailed description of the invention.

SUMMARY OF THE INVENTION

The foregoing objects and other features and advantages of the present invention are achieved by detergent and cleansing compositions comprising a synergistic mixture of surfactants which exhibit low eye and skin irritancy and good foam properties. More specifically, the present invention relates to detergent and cleansing compositions comprising a synergistic mixture of a specific amphoteric-fatty acid complex and specific anionic surfactants containing at least one carboxylic acid moiety.

DETAILED DESCRIPTION OF THE INVENTION

In general, this invention comprises a synergistic mixture of a specific amphoteric-fatty acid complex and a specific anionic surfactant in a ratio of from about 1:4 to 4:1. The term "synergistic mixture" as used herein refers to a mixture of two discrete compounds which display a degree of initial foam height and quality which is greater than the sum of the initial foam heights of the compounds taken individually.

The specific amphoteric-fatty acid complexes which have been found useful in the present invention are non-zwitterionic in nature and are of the formula

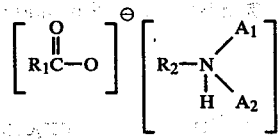

wherein $R_1$ is alkyl or substituted alkyl containing from about 5 to 17 carbon atoms and mixtures thereof.

$R_2$ is alkyl containing from about 6 to 18 carbon atoms and mixtures thereof or alkyl amido of the formula

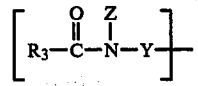

wherein $R_3$ is alkyl containing from about 5 to 17 carbon atoms, Z is H or lower alkyl containing from 1 to 4 carbon atoms; and Y is alkylene containing from 2 to 4 carbon atoms;

$A_1$ and $A_2$ are the same or different and at least one of $A_1$ and $A_2$ are selected from the group of anionic salt moieties consisting of the following:

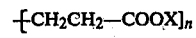

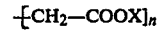

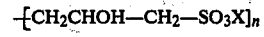

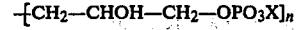

wherein X is a water soluble cation such as $Na^+$, $K^+$, $Ca^{++}$, $Mg^{++}$ and the like and n is an integer of 1 or 2 with the proviso that if only one of $A_1$ and $A_2$ are selected from the anionic salt moieties above the other can be lower alkyl or lower hydroxyalkyl containing from 1 to 4 carbon atoms.

The amphoteric-fatty acid complexes which are useful in the present invention are novel compounds described and claimed in copending patent applications Ser. No. 241,862 filed Mar. 9, 1981, now abandoned and Ser. No. 375,073 filed May 5, 1982 and can be prepared in accordance with the processes described therein; the teachings of said copending applications are incorporated herein by reference.

Representative amphoteric-fatty acid complexes useful in the present invention include the following:

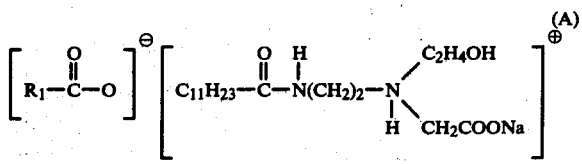
(A)

wherein $R_1$ is a mixture of alkyl chain lengths of from $C_5H_{11}$–$C_{17}H_{35}$.

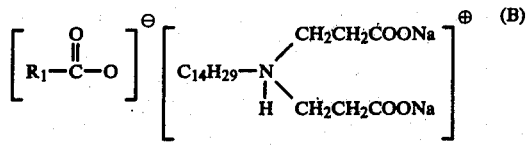
(B)

wherein $R_1$ is an 80%/20% mixture of tallow and coconut alkyl chain lengths.

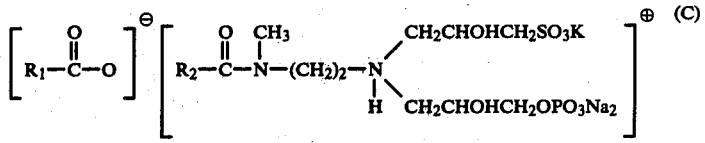
(C)

wherein $R_1$ is tallow alkyl chain lengths and $R_2$ is a $C_{11}H_{23}$–$C_{17}H_{35}$ mixture.

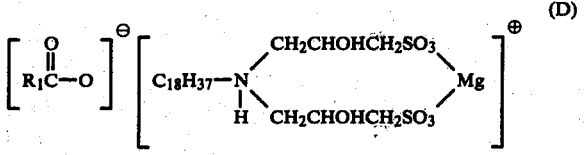
(D)

wherein $R_1$ is a 70%/30% mixture of lauric and myristic alkyl chain lengths.

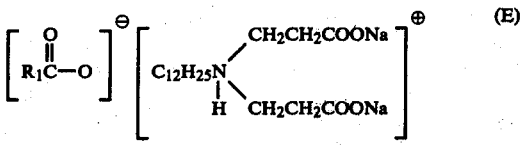
(E)

wherein $R_1$ is tallow alkyl chain lengths.

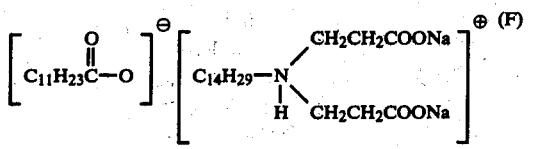
(F)

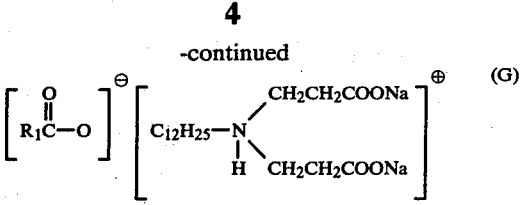
(G)

wherein $R_1$ is a mixture of alkyl chain lengths of from $C_5H_{11}$–$C_{17}H_{35}$.

The amphoteric-fatty acid complexes useful in the compositions of this invention are present in an amount of from about 1 to 50% by weight of the total composition, preferably about 5 to 15% by weight of the total composition.

The specific anionic surfactants which have been found useful in the present invention are those containing at least one carboxylic acid moiety and are selected from the group consisting of alkyl sulfosuccinates, alkyl ether carboxylates, α-sulfo fatty acid and ester carboxylates, alkyl succinates, acyl sarcosinates and fatty acid protein condensates. All of these compounds are well known in the art and can then be prepared according to well-recognized processes.

The alkyl sulfosuccinates are of the general formula

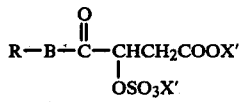

and can be prepared by reacting maleic acid with a suitable fatty alcohol followed by the addition of NaHSO₃ to the double bond.

The α-sulfo fatty acid and ester carboxylates are of the following general formuli respectively

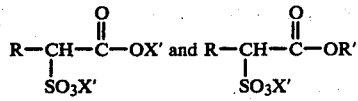

and can be prepared by sulfonation of the suitable fatty acids and esters.

The alkyl ether carboxylates are of the following general formula

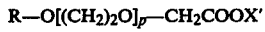

and these compounds can be prepared by the Williamson ether synthesis which involves reacting an alkoxide with sodium chloroacetate.

The alkyl succinates are of the general formula

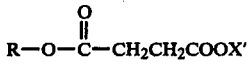

and are the reaction product of a suitable fatty alcohol with succinic acid or succinic anhydride.

The acyl sarcosinates are of the general formula

and are the reaction product of a suitable fatty acid with a lower substituted amine such as glycine or N-methyl glycine.

The fatty acid protein condensates are of the general formula

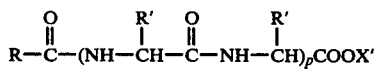

and are the reaction products of a suitable fatty acid with an amino hydrolysate.

In the above specific anionic surfactants R is alkyl containing from about 8 to 17 carbon atoms; R' is lower alkyl of from about 1 to 5 carbon atoms; B is O, N or O—$(CH_2—CH_2O)_m$ wherein m is an integer of from 1 to 5; X' is H+ or a water soluble cation such as Na+, K+, Ca++, Mg++ and the like; p is an integer of from 1 to 100; and Z is as defined above.

Specific examples of suitable anionic surfactants include:

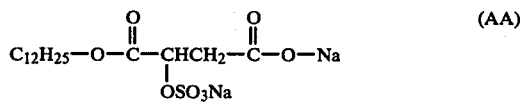 (AA)

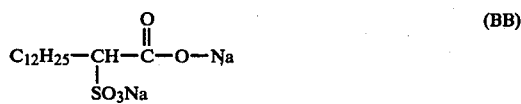 (BB)

 (CC)

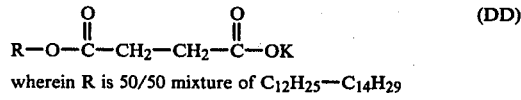 (DD)

wherein R is 50/50 mixture of $C_{12}H_{25}$—$C_{14}H_{29}$ $C_{13}H_{27}$—O—$[(CH_2)_2O]_4$—$CH_2COONa$ (EE)

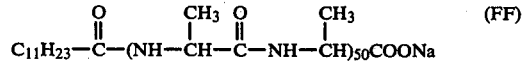 (FF)

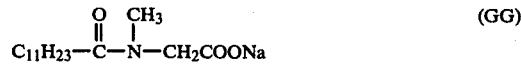 (GG)

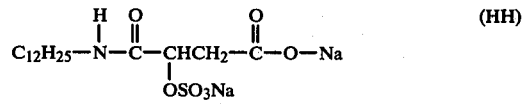 (HH)

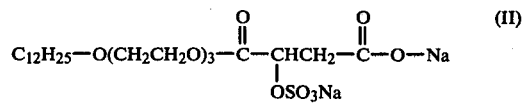 (II)

The anionic surfactants useful in the compositions of this invention are present in an amount of from about 2 to 50% by weight of the total composition.

Further, to achieve the desired results of the present invention, the amphoteric-fatty acid complex and the specific anionic surfactant should be in a ratio of from about 4:1 to 1:4, preferably from about 2:1 to 1:2.

In preparing various formulations and compositions, if desired and if compatible, various other surfactants can be utilized such as other anionics, nonionics, amphoterics, cationics and the like. In addition to such other surfactants, other ingredients conventionally added to detergent and cleansing compositions for personal use, such as dyes, preservatives, perfumes, thickeners, opacifiers, conditioners, emollients, buffering agents and the like, may be added in minor amounts. Ingredients such as dyes, preservatives and perfumes together usually constitute less than 2% by weight of the total composition.

The detergent and cleansing compositions of the present invention may be in the form of liquid detergent compositions or detergent bar compositions, as desired.

Liquid detergent formulations utilizing the compositions of the present invention can be prepared by admixing the amphoteric-fatty acid complex and anionic surfactant at room temperature or slightly elevated temperatures (about 50° C.) and then sufficient deionized water is added to bring the composition to about three quarters of its intended weight. Other ingredients such as other surfactants, various detergency adjuncts, fillers, carriers, perfumes, preservatives, gelling agents and the like are added as required followed by the balance of the water.

The pH is then adjusted to within a range of about 6.5 to 8.5 by the addition of strong acid, e.g., HCl, or strong based NaOH, as needed.

Detergent for formulations utilizing the compositions of the present invention can be prepared by admixing the amphoteric-fatty acid complex and the anionic surfactant in a steam jacketed rotary mixer at temperatures within the range of 60°-80° C. Other surfactants, fillers, whitening agents and processing oils can be added, as needed, to the hot slurry. The pH is then adjusted to within the range of about 6.5 to 8.5 by the addition of strong acid or strong base as needed. After adequate mixing to assure homogeneity and moisture balance the product is chill rolled or drum dried into flakes. Dyes and fragrances are added to the flakes in a standard amalgamator together with additional water to provide proper bar formation. After adequate mixing the flakes are milled and plodded into logs which are then cut into blanks prior to stamping into bar form.

The detergent compositions of the present invention can be tested for ocular irritation by the following modified Draize Test (J. H. et al., Toilet Goods Assn. No. 17, May 1952, No. 1, Proc. Sci. Sect.).

An 0.1 ml. sample of a neutral composition under test is dropped into one eye of an albino rabbit, the other eye serving as a control. Six rabbits are employed for each composition. Observations are made after 1, 24, 48, 72 and 96 hours and 7 days after initial instillation; second and third instillations are made after the 24 and 48 hour readings. Results may vary from substantially no change or only a slight irritation in the appearance of the rabbit's eye after 7 days to severe irritation and/or complete corneal opacity. Ocular lesions are scored for the cornea, iris and conjunctiva with a higher number indicating greater ocular irritation and the scores are added to give a total numerical value for each reading for six rabbits and averaged. The averaged score is an indication of the irritation potential of the composition under test. Based on the averaged score, descriptive irritation evaluation may be given, e.g., none, slight, moderate, severe, as the case may be.

Detergent compositions of the invention provide high foam volume and moreover outstanding foam stability as measured by an adaption of the well-known Ross-Miles foam test principle "Oil and Soap" 18.9–102 (1941):

Lanolin, anhydrous, cosmetic grade is mixed with dioxane (technical grade) in the proportion of 2.5 grams lanolin and 100 grams of dioxane. The lanolin is first mixed with 25 cc. of dioxane. This mixture is heated over a steam bath to 45° C. in order to dissolve the lanolin in the dioxane. The remainder of the dioxane is then added and mixed. This lanolin dioxane solution, which is stored in an amber bottle, should be prepared fresh on the day that the tests are run.

The composition to be tested is diluted by adding 376 cc. of distilled water to 4 grams of the composition, and then by adding 20 cc. of the lanolin dioxane solution described above while mixing. Heat is produced when the lanolin dioxane solution is added to the solution of the composition in water and care must be taken in adjusting the temperature of this solution to 24°–25° C. Both of these intermediate solutions should therefore be adjusted to 23° C. before mixing. The cooling of the lanolin dioxane solution should be gradual in order to avoid precipitation of the lanolin. This will produce a final solution with a temperature of 24°–25° C.

The final solution of the composition to be tested, water, dioxane and lanolin described above, is then run in a modified Ross-Miles foam column in the usual way. All tests are conducted in duplicate, and the average of the two results is taken. Foam stability is determined by measuring the decay in foam height after two minutes, expressed as a percentage of the original height.

Specific embodiments of the present invention are illustrated by the following representative examples. It will be understood, however, that the invention is not confined to the specific limitations set forth in the individual examples, but rather to the scope of the appended claims.

EXAMPLES I–IX

The following compositions are prepared by admixing the surfactant components, adjusting the pH to 7.2±0.2 with dilute acid or base as required and adding deionized water to 100%:

| | % wt/wt. EXAMPLES | | | | | | | | |
|---|---|---|---|---|---|---|---|---|---|
| | I | II | III | IV | V | VI | VII | VIII | IX |
| Compound B | 5.0 | | | | | 2.5 | 2.5 | 2.5 | 2.5 |
| lauryl succinic acid | | 5.0 | | | | 2.5 | | | |
| disodium sulfococoate | | | 5.0 | | | | 2.5 | | |
| lauryl ether (4) carboxylate | | | | 5.0 | | | | 2.5 | |
| lauryl disodium sulfosuccinate | | | | | 5.0 | | | | 2.5 |
| deionized water | q.s. to 100% | | | | | | | | |

EXAMPLE X

The compositions prepared in Examples I–IX are tested for hard water foam properties using the modified Ross-Miles procedure set forth hereinbefore and the results are as follows:

| Example | Initial Foam Height in mm - 200 ppm hard water |
|---|---|
| I | 358 |
| II | 330 |
| III | 348 |
| IV | 330 |
| V | 330 |
| VI | 365 |
| VII | 375 |
| VIII | 368 |
| IX | 378 |

As can be readily seen from the results above, the compositions containing a mixture of the specific amphoteric-fatty acid complexes and the anionic surfactants of the present invention (Examples VI–IX) exhibit a synergistic increase in initial foam height. It is also observed that the quality of the foam generated by the compositions of the present invention is superior to that of the other compositions in that it is denser and creamier. A generated foam of this nature is not only perceived to be better by the consumer, but is also capable of supporting and suspending soils in a manner superior to the more open, lace-like foam of the compositions of Examples I–V and thus these soils are more easily removed.

EXAMPLE XI

A detergent bar composition is prepared by charging to a steam-jacketed rotary mixer 23.7 parts by weight stearic acid, 13.3 parts by weight dextrin, 35.1 parts by weight disodium α-sulfococoate, 14.2 parts by weight compound A, 0.2 parts titanium dioxide and 10.0 parts water. The mixture is heated to 50°–60° C. and mixed until homogeneous and the pH is adjusted to 7.2±0.2 with 50% NaOH solution. The resulting product is chilled, rolled in flakes, milled, plodded and stamped into bars having the following composition:

| | % wt/wt |
|---|---|
| stearic acid | 23.7 |
| dextrin | 13.3 |
| disodium α-sulfococoate | 35.1 |
| Compound A | 14.2 |
| TiO$_2$ | 0.2 |
| 50% NaOH | 5.2 |
| deionized water | 8.3 |
| | 100.0 |

The resulting bar foams copiously in hard and soft water and free of lime soap deposits and is also found to be a slight ocular irritant when tested.

EXAMPLE XII

A detergent bar composition is prepared in accordance with the procedure of Example XI and has the following formulation:

| | % wt/wt |
|---|---|
| Compound B | 20.00 |
| stearic acid | 15.00 |
| polyethylene glycol 4000 | 5.00 |
| dextrin | 10.00 |
| talc | 10.00 |
| disodium lauryl sulfosuccinate | 35.00 |
| deionized water | 5.00 |
| | 100.00 |

The pH is adjusted to about 6.5 utilizing 50% NaOH solution.

EXAMPLE XIII

A liquid cream soap product is prepared as follows: 87.5 parts by weight of compound C and 20.0 parts by weight of lauryl succinic acid are charged to a vessel equipped with a stirrer and steam and are heated to 45° C. The pH is adjusted to 7.0±0.2 with dilute NaOH followed by the addition of 1 part of propylene glycol and 95 grams of deionized water. The mass is cooled to 30° C. and 2 parts of a fragrance are added prior to filling into tubes. The resulting product has the following formulation:

|  | % wt/wt |
|---|---|
| Compound C | 42.57 |
| lauryl succinate | 9.73 |
| propylene glycol | 0.48 |
| fragrance | 0.97 |
| deionized water | q.s. to 100% |

The product is a smooth opaque mild cream gel easily dispensed from tubes.

EXAMPLE XIV

An opaque liquid soap is prepared having the following formulation:

|  | % wt/wt |
|---|---|
| Compound D | 30.0 |
| lauroyl sarcosinate | 20.0 |
| polyethylene glycol 6000 distearate | 3.0 |
| deionized water | q.s. to 100 |

The pH of the above formulation is adjusted to 6.5 with dilute HCl.

EXAMPLE XV

An opaque liquid soap is prepared having the following formulation:

|  | % wt/wt |
|---|---|
| disodium lauryl sulfosuccinate | 3.00 |
| Compound A | 2.50 |
| ammonium lauryl (3) ether sulfate | 3.00 |
| polyoxyethylene 80 sorbitan monolaurate | 5.00 |
| preservative | .10 |
| dye and fragrance | .25 |
| deionized water | q.s. to 100 |

The pH of the above formulation is adjusted to 6.5 with dilute HCl.

EXAMPLE XVI

A conditioning shampoo composition is prepared having the following formulation:

|  | wt/wt % |
|---|---|
| Compound A | 7.45 |
| sodium lauryl sulfate | 6.60 |
| disodium lauryl sulfosuccinate | 5.80 |
| Dowicil 200 | .10 |
| hydroxypropylmethylcellulose | .50 |
| sodium chloride | .50 |
| ethylene glycol monostearate | .60 |
| polyoxyethylene (80) sorbitan monolaurate | .18 |
| dye | .01 |
| tetra-sodium salt of ethylenediamine tetraacetic acid | .06 |
| fragrance | .50 |
| deionized water | q.s. to 100 |

The above formulation is adjusted to a pH about 7.8±0.1 with HCl or NaOH as needed and has a viscosity of about 4000 cps. at 25° C. and is a slight ocular irritant. The formulation exhibits excellent foaming and conditioning properties.

In addition to the preferred embodiments described herein, other embodiments, arrangements, and variations within the spirit of the invention and the scope of the appended claims will occur to those skilled in the art.

We claim:

1. A low irritating detergent and cleansing composition wherein the active ingredients consist essentially of
   (a) from about 1 to 50% by weight of an amphoteric-fatty acid complex of the formula

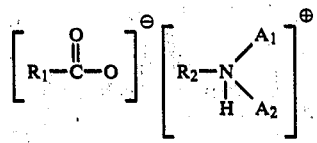

wherein $R_1$ is alkyl or substituted alkyl containing from about 5 to 17 carbon atoms and mixtures thereof; $R_2$ is alkyl containing from about 6 to 18 carbon atoms and mixtures thereof or alkyl amido of the formula

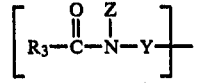

wherein $R_3$ is alkyl containing from about 5 to 17 carbon atoms, Z is H or lower alkyl containing from 1 to 4 carbon atoms; and Y is alkylene containing from 2 to 4 carbon atoms;

$A_1$ and $A_2$ are the same or different and at least one of $A_1$ and $A_2$ are selected from the group of anionic salt moieties consisting of the following:

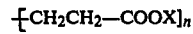

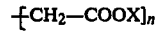

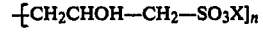

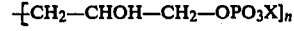

wherein X is a water soluble cation and n is an integer of 1 or 2 with the proviso that if only one of $A_1$ and $A_2$ are selected from the anionic salt moieties above the other is lower alkyl or lower hydroxyalkyl containing from 1 to 4 carbon atoms; and (b) from about 2 to 50% by weight of an anionic surfactant selected from the group consisting of alkyl sulfosuccinates of the formula

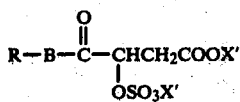

alkyl ether carboxylates, α-sulfo fatty acids of the formula

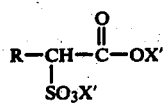

alkyl succinates, acyl sarcosinates and fatty acid protein condensates; wherein R is alkyl from 8 to 17 carbon atoms, X' is hydrogen or a water soluble cation and B is O, N or $O\text{-}(C_2\text{--}CH_2O)_m$ wherein m is an integer of from 1 to 5; and wherein the amphoteric-fatty acid complex and the anionic surfactant are in the ratio of from about 1:4 to 4:1.

2. The composition of claim 1 wherein the amphoteric-fatty acid complex is of the formula

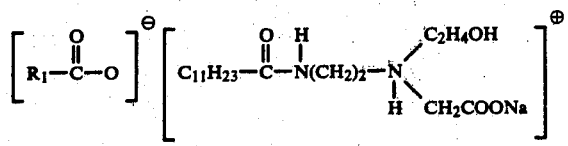

wherein $R_1$ is a mixture of alkyl chain lengths of from $C_5H_{11}$–$C_{17}H_{35}$.

3. The composition of claim 1 wherein the amphoteric-fatty acid complex is of the formula

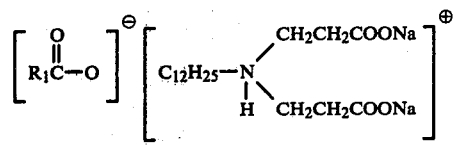

wherein $R_1$ is a mixture of alkyl chain lengths from $C_5H_{11}$–$C_{17}H_{35}$.

4. The composition of claim 1 wherein the amphoteric-fatty acid complex is of the formula

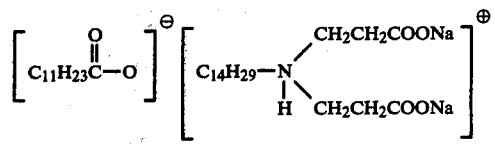

5. The composition of claim 1 wherein the amphoteric-fatty acid complex is from about 5 to 15% by weight of the total composition.

6. The composition of claim 1 wherein the anionic surfactant is an acyl sarcosinate.

7. The composition of claim 1 wherein the anionic surfactant is a alkyl sulfosuccinate.

8. The composition of claim 1 wherein the anionic surfactant is an alkyl succinate.

9. The composition of claim 1 wherein the anionic surfactant is from about 5 to 40% by weight of the total composition.

* * * * *